United States Patent [19]

New

[11] Patent Number: 5,853,748
[45] Date of Patent: Dec. 29, 1998

[54] PHARMACEUTICAL COMPOSITIONS

[75] Inventor: Roger Randal Charles New, London, United Kingdom

[73] Assignee: Cortecs (UK) Limited, United Kingdom

[21] Appl. No.: 804,508

[22] Filed: Feb. 24, 1997

Related U.S. Application Data

[63] Continuation-in-part of PCT/GB95/02015 Aug. 25, 1995.

[30] Foreign Application Priority Data

Aug. 31, 1994 [GB] United Kingdom .................... 9417524

[51] Int. Cl.[6] ............................... A61K 9/00; A61K 9/20; A61K 9/14
[52] U.S. Cl. ......................... 424/439; 424/400; 424/464; 424/489; 424/491
[58] Field of Search .................................. 424/464, 489, 424/491, 439

[56] References Cited

FOREIGN PATENT DOCUMENTS

| A 0127535 | 12/1984 | European Pat. Off. . |
| A 0509335 | 10/1995 | European Pat. Off. . |
| A 4234537 | 4/1994 | Germany . |
| 900271447 | 5/1992 | Japan . |
| 2 244 918 | 12/1991 | United Kingdom . |
| WO 90/12583 | 11/1990 | WIPO . |

OTHER PUBLICATIONS

Wosiewitz et al., J. Hepatology, 14:7–15(1992).
Wosiewitz et al., *Chemical Abstracts*, vol. 116, #143793 1992.
Kakemi et al., Chem. Pharm. Bull., 18(2:275–280 (1970).
Kojima et al., Chem. Pharm. Bull., 25(6):1243–1248 (1977).

*Primary Examiner*—Thurman K. Page
*Assistant Examiner*—S. Howard
*Attorney, Agent, or Firm*—Pennie & Edmonds LLP

[57] ABSTRACT

Compositions containing a bile salt and a buffer such as a carbonate or bicarbonate salt which is adapted to buffer the gut to a pH of from 7.5 to 9 are capable of increasing the bioavailability of an active molecule whilst minimising the toxic side effects which are generally associated with bile salts.

19 Claims, 7 Drawing Sheets

PHARMACEUTICAL COMPOSITIONS

This application is a continuation of PCT/GB95/02015 filed Aug. 25, 1995.

The present invention relates to pharmaceutical compositions and, in particular to orally administrable compositions of proteins, peptides and other active molecules which are not generally easily absorbed from the gastrointestinal tract.

Medical practice has for many years prescribed or advised the administration of many biologically active materials for the treatment or prophylaxis of a wide variety of diseases or conditions. One of the most well known, but by no means the only, prescribed biologically active proteinaceous material is insulin, which is used for the control of diabetes. Other biologically active proteinaceous materials include growth factors, interleukins and calcitonin and non-proteinaceous biologically active materials include oligonucleotides and polysaccharides.

Possibly the easiest method of taking any medication is oral ingestion. Such route of administration, which may be by means of syrup, elixir, tablets, capsules, granules, powders or any other convenient formulation, is generally simple and straightforward and is frequently the least inconvenient or unpleasant route of administration from the patient's point of view.

It is therefore unfortunate that most of these materials are very poorly absorbed when administered orally. Firstly, the preferred route of administration of proteinaceous medicaments and other biologically active materials involves passing the material through the stomach, which is a hostile environment for many materials, including proteins. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine.

It is possible to provide enteric coated formulations which are protected from the acid environment of the stomach but even so, relatively large molecules such as peptides and proteins are poorly absorbed by the small intestine.

The result, as many diabetics can testify, is that many proteinaceous medicaments have to be taken parenterally, often by subcutaneous, intramuscular or intravenous injection, with all the inconvenience, discomfort and difficulties of patient compliance that that entails.

This is not an isolated problem, as diseases needing control by the administration of proteinaceous material can be very widespread. Diabetes, for example, claims a large number of sufferers in many countries of the world and there are numerous other conditions which require treatment by administration of a proteinaceous compound or another macromolecule. Osteoporosis is another example of a condition which can be treated using a protein—in this case calcitonin—and protein growth hormones can be used to treat dwarfism.

Clearly, therefore, there is a need for pharmaceutical formulations of proteins and other macromolecules which can be administered orally and which provide acceptable bioavailability of the active material.

It is known that when pharmaceutically active compounds are administered together with certain bile salts, their bioavailability is increased. This is discussed by Kakemi et al, (*Chem. Pharm. Bull*, 18(2) 275–280 (1970)) who showed that the bioavailability of various substances could be increased by administration in combination with taurocholate or glycocholate. Further experiments by Kojima et al (*Chem. Pharm. Bull*, 25(6) 1243–1248 (1977)) showed that sodium cholate is capable of increasing the absorption of various substances but that release of cell membrane components is also accelerated.

In addition there are several other references in the prior art to the use of bile salts as absorption enhancers including GB-A-2244918 which teaches that the bioavailability of somatostatin can be improved when it is administered with a cholanic acid derivative such as chenodeoxycholic acid or ursodeoxycholic acid.

It is believed that the bile salts improve absorption of biologically active materials because of their action on the cell membranes of epithelial cells. The cell membranes become more permeable, possibly because the detergent action of the bile salts removes lipids from cell membranes and causes them to become more fluid. One theory is that the increased permeability of the cell membrane enables the active materials to pass through the epithelial cells. Alternatively, it is possible that the cytoskeletal structure of the epithelial cells is modified as a result of changes in cytoplasmic levels of sodium or calcium arising from increased membrane permeability. This would result in alteration of the integrity of the tight junctions so that there are gaps between the cells through which the active materials can pass. Whatever the mechanism, it seems clear that the increased absorption arises from the increased permeability of the cell membranes.

However the inclusion of bile salts in pharmaceutical formulations has always been a problem because they have unacceptably high toxicity when used in the amounts required for them to exert their bioavailability improving effect. It has been suggested that the reason for this is that the increase in the permeability of epithelial cells brought into contact with bile salts results in an increased flow of ions into and out of the cell. In order for cells to remain viable, the intracellular concentrations of ions such as sodium, potassium and calcium ions must remain within relatively narrow ranges and it may be that the increased ion flow caused by the presence of bile salts causes the intracellular ion concentrations to move outside the ranges within which cells are viable. Thus, the problem with the use of bile salts as absorption enhancers is that they have always been considered to have an unacceptably low therapeutic index. Throughout the present specification the term "therapeutic index" has been used to refer to the ratio toxic dose: absorption enhancing dose.

It would thus be extremely useful to be able to reduce the toxicity and hence effectively to increase the therapeutic index of bile salts to the point where they could be used in pharmaceutical compositions without unacceptable toxic side effects.

In a first aspect of the present invention there is provided a pharmaceutical and/or veterinary composition comprising a biologically active material, a bile acid or salt and an agent adapted to adjust the pH of the gut to a pH value of from 7.5 to 9.

WO-A-9012583 teaches a pharmaceutical composition comprising an active agent, a bile salt and an additional component of bile. However, the only additional components suggested in this document as likely to be useful in such compositions are additional bile salts and biliary lipids, in particular phospholipids. Although bicarbonate (a preferred pH adjusting agent useful in the invention) is a component of bile, there is no mention of bicarbonate salts in WO-A-9012583 and it is clear that bicarbonate salts were not envisaged as being useful components of a composition containing a bile salt and a pharmaceutically active agent. Thus the effect of bicarbonate or other pH adjusting agents in effectively increasing the therapeutic index of bile salts was certainly not disclosed in this prior document.

In the present invention it should be understood that the terms bile salt and bile acid are used inter-changeably because whether the salt or its conjugate acid is present will depend on the pH of the surrounding environment. Thus, solid formulations according to the invention may contain either a bile salt or a bile acid. However, the compositions as administered will often be of a pH such that if an acid is used, it will be converted into the salt form when in solution.

When a bile salt is used in the compositions of the present invention, it is preferred that there is a soluble counter-ion present such as sodium or potassium. It is also possible to use, for example, an ammonium ion but this is less preferred.

Bile salts are naturally occurring surfactants. They are a group of compounds with a common "backbone"0 structure based on cholanic acid found in all mammals and higher vegetables. Bile salts may be mono-, di- or tri-hydroxylated; they always contain a 3α-hydroxyl group whereas the other hydroxyl groups, most commonly found at $C_6$, $C_7$ or $C_{12}$, may be positioned either above (β) or below (α) the plane of the molecule.

Within the class of compounds described as bile salts are included amphiphilic polyhydric sterols bearing carboxyl groups as part of the primary side chain. The most common examples of these in mammals result from cholesterol metabolism and are found in the bile and, in derivatised form, throughout the intestine.

In the context of this specification, the term may also apply to synthetic analogues of naturally occurring bile salts which display similar biological effects, or to microbially derived molecules such as fusidic acid and its derivatives.

The bile salt may be either unconjugated or conjugated. The term "unconjugated" refers to a bile salt in which the primary side chain has a single carboxyl group which is at the terminal position and which is unsubstituted. Examples of unconjugated bile salts include cholate, ursodeoxycholate, chenodeoxycholate and deoxycholate. A conjugated bile salt is one in which the primary side chain has a carboxyl group which is substituted. Often the substituent will be an amino acid derivative which is linked via its nitrogen atom to the carboxyl group of the bile salt. Examples of conjugated bile salts include taurocholate, glycocholate, taurodeoxycholate and glycodeoxycholate.

The quantity of bile acid contained in a single dose of the formulation will vary depending on the particular bile acid chosen and the rate and extent to which that bile acid dissolves in the aqueous fluid contained in the intestine. For chenodeoxycholic acid, and most other bile acids, this is likely to be within the range 10 mg to 1 g, preferably between 20 mg to 200 mg, and most preferably 30 mg to 100 mg. For deoxycholic acid, the maximum will generally not exceed 500 mg, in view of its slightly greater activity.

The gut of many animals (particularly humans and other mammals) is naturally buffered to a pH below neutrality. Compositions of the invention comprise an agent adapted to adjust the pH of the gut to a pH of from 7.5 to 9. The agent is "adapted" to adjust the pH either by its chemical nature or by the amount in which it is present or, usually, both. The optimum pH to which the gut is adjusted is in the range 7.8 to 8.3.

While simple agents adapted to adjust the pH of the gut into the range specified above may be successfully used in the invention, it is preferred that the pH adjusting agent also has the capability of buffering the gut to a pH within the stated range. This can give a more long lasting effect, which may be desired in many circumstances. Also, a buffer has a greater capacity to accommodate the patient-to-patient variability of endogenous gut pH, as well as the viability of gut pH seen over time in any individual patient; in particular, a buffer can act as a safety barrier to ensure that the pH of the patient's gut is not radically changed outside safe limits during the administration of formulations of the invention.

Two of the most favoured agents for adjusting the pH suitable for use in the invention, either separately or in combination, are carbonate and bicarbonate ions. In the discussion which follows, bicarbonate is referred to by way of illustration of the principles involved, but the same principles apply equally to other agents capable of exerting a similar effect on intestinal pH.

The amount of agent necessary to adjust the pH to within the range contemplated is difficult to determine directly because the intestinal pH can vary between 5 to 7, and its aqueous content can vary, as can its intrinsic buffering capacity, which acts to maintain a low pH. Consequently considerations aimed at determining the appropriate quantity of agent controlling pH need to take into account a "worst-case" scenario. An indication may be obtained by observing the pH achieved upon adding a potential pH-adjusting agent to a 50 mM solution of MES (morpholino ethane sulphonic acid) adjusted to pH 6.0. Concentrations useful in the invention are those that result in the adjustment of the pH to within the range 7.5 to 9; preferred concentrations result in an adjustment to within the range 7.8 to 8.3. (For reasons which will be explained below, the weight amount of pH adjusting agent is generally that which produces the desired concentration in 10 ml liquid.) Values for pH attained are shown below for the preferred bicarbonate at different concentrations, dispersed in distilled water or in MES.

| Bicarbonate concentration (molarity) | Water | MES |
|---|---|---|
| 0.002 | 8.86 | 6.42 |
| 0.004 | 8.67 | 6.58 |
| 0.008 | 8.63 | 6.86 |
| 0.016 | 8.57 | 7.14 |
| 0.031 | 8.55 | 7.40 |
| 0.062 | 8.49 | 7.68 |
| 0.125 | 8.41 | 7.93 |
| 0.250 | 8.30 | 8.14 |
| 0.500 | 8.16 | 8.05 |
| 1.000 | 8.02 | 7.96 |

Hence, the minimum amount of bicarbonate useful in the invention in most cases is about 0.045M, which yields a pH in the gut of about 7.5. This translates to about 40 mg sodium bicarbonate, for a 10 ml dispersion volume.

A saturated solution of bicarbonate in water (<2M) has a pH of 8.01. From this it will be seen that, regardless of the concentration of preferred bicarbonate administered, the pH will not rise above 9.0. Under certain circumstances, it may be that a concentrated solution of a salt of the bile acid itself has sufficient capacity to raise the pH to the appropriate level, although the effect will not be as strong as for the preferred bicarbonate. Hence, it is possible, although not always desirable, for the pH adjusting agent to be the bile salt itself, or a different bile salt.

The greater the buffering capacity of the composition, the longer that the pH specified above will prevail in the gut and hence the longer the benefits of the invention will prevail.

Two of the most favoured buffering agents suitable for use in the invention, either separately or in combination, are carbonate and bicarbonate ions. As already mentioned, the advantage of the compositions of the present invention is that they are capable of effectively increasing the therapeutic index of the bile salt present in the composition. The beneficial effect is present both for conjugated and unconjugated bile salts but the action of the carbonate or bicarbonate ions on conjugated bile salts is slightly different from the action on unconjugated bile salts.

With conjugated bile salts, the presence of sufficient bicarbonate or carbonate has the effect of increasing cell membrane permeability during the exposure of cells to a given amount of bile salt without affecting cell viability. This means that the amount of bile salt needed to obtain a given increase in permeability is reduced and so the permeability of the cells can be increased without increasing the adverse effects of the bile salt.

With unconjugated bile salts in the presence of carbonate or bicarbonate, cell permeability is not increased during exposure of the cell to the bile salt but, rather, the toxic effect on cells after exposure to bile salt is reduced. Again, this means that the amount of bile salt which can be administered without affecting the viability of the cells is increased in the presence of bicarbonate or carbonate ions.

In general, the amount of pH adjusting agent will be such that when a unit dose of the composition is dispersed in the amount of liquid which would be present in the length of gut over which the composition would be distributed on administration to a patient, the pH adjusting agent concentration is at least about 0.01M, although a more precise estimate can be had by reference to the MES buffer test referred to above. Usually, and preferably for carbonate and bicarbonate, however, the concentration of bicarbonate or carbonate will be greater than 0.05M and it is most preferred that the concentration is at least about 0.1M although higher concentrations, for example up to 1M can be used.

A typical length of the small intestine over which a composition of the present invention would be likely to be distributed would be 30 cm and the amount of liquid which would be present in that length of gut would be likely to be about 10 ml. However, it should be stressed that the choice of 30 cm as a suitable length is arbitrary and the invention is not intended to be limited to compositions which are distributed over this distance in the small intestine. There may be reasons why it would be desirable for a composition to be distributed over a shorter or a much longer period of time, for example a sustained release composition may disperse much more slowly and would therefore be distributed over a much longer length of the small intestine. Such compositions are familiar to those skilled in the art who would easily be able to determine the most suitable type of composition to meet a particular therapeutic requirement.

If the composition were adapted to be dispersed over a longer or shorter length of the small intestine then the amount of water in which a unit dose of the composition would be dispersed to give a particular concentration would be accordingly greater or smaller.

The unit dose which is dispersed in water to determine the minimum amount of bicarbonate required will be the dose which would be administered to a patient at any one time. For liquid formulations, this will be a predetermined amount calculated by a physician or pharmacist. For solid formulations, such as tablets or capsules, the unit dose will generally be a single tablet or capsule. However, there may be circumstances in which a patient would be required to take more than one tablet or capsule, for example if large doses of active substance are needed, and in this case the amount of bicarbonate may be divided between two or more tablets or capsules.

It appears that an additional beneficial effect of the preferred carbonate or bicarbonate ions may arise because they can increase the solubility of the bile acids. In general bile salts start to be converted to their conjugate acid at pH of about 6.8 or below and the acid form is insoluble in aqueous solutions. Since the buffering agent has the effect of buffering the compositions of the invention to a pH of about 7.5 or above, the solubilised bile salt will be present rather than the insoluble bile acid. A solubilised bile salt will be able to act on the epithelial cells when in solution, whereas this may not be possible in the solid acid form. The higher the concentration of buffering agent, the more rapidly will a satisfactory pH be attained, resulting in more rapid dissolution of the bile acid or salt; this will result in a higher local concentration of the bile salt in solution, leading to greater efficacy in enhancing permeability to bioactive materials.

It is also possible that the reason for the particularly beneficial effect of carbonate and bicarbonate ions is associated in some way with the fact that bicarbonate receptors are expressed on the surfaces of intestinal cells. However, the nature of this link, if indeed it exists, is not clear at present and, in any case, it should be stressed that the correctness or otherwise of this theory does not limit the effectiveness of the present invention. The results obtained using bicarbonate are generally superior.

As discussed above, it is thought that one of the functions of the bicarbonate or carbonate ions is to ensure that the bile salt is in the soluble form. However, the presence of calcium ions increases the pH at which the salt becomes the prevalent form and below which insoluble bile acid will start to precipitate out of solution. This pH varies according to the particular bile salt but it is desirable to prevent precipitation of the bile acid. For this reason, it is often advantageous to include in the composition a chelator of calcium ions such as a salt of a di- or tri-carboxylic acid (for example a citrate salt), ethylenediaminetetraacetic acid (EDTA), ethylene glycol bis-($\beta$-aminoethylether)N,N,N',N'-tetraacetic acid (EGTA) or phytate and other polyphosphorus compounds.

When a citrate salt is used as the calcium ion chelator, it is greatly preferred that it should be in a form soluble in water. The most suitable salts are therefore sodium and potassium citrate although in some circumstances ammonium citrate may also be used.

The term "biologically active material" includes, in particular, pharmaceutically active proteinaceous materials. The proteinaceous material may be a pure protein, or it may comprise protein, in the way that a glycoprotein comprises both protein and sugar residues.

The material may be useful in human or veterinary medicine, either by way of treatment or prophylaxis of diseases or their symptoms, or may be useful cosmetically or diagnostically. Examples of proteinaceous biological material which can be provided as orally or rectally administrable formulations in accordance with this invention include protein or peptide hormones or hormone releasing factors such as insulin, calcitonin and growth hormone, whether from human or animals or semi- or totally synthetically prepared, or other bioactive peptides such as interferons including human interferon alpha and interleukins including IL-1, IL-2, IL-3, IL-4 and IL-5. Analogues and active fragments of these or other proteins may also be used.

It is particularly remarkable that the invention not only works, but works well, with insulin, as insulin is normally poorly soluble at the pH values contemplated by the present invention. It seems that the insulin is only able to disperse as a result of some unexpected interaction between insulin and bile salt which stabilises it in bicarbonate or other high pH solution.

Biologically active materials may also be oligonucleotides such as antisense oligonucleotides and their analogues which may be useful for interfering with the replication of nucleic acids in virally infected or cancerous cells and for correcting other forms of inappropriate cell proliferation. Polysaccharides such as heparin are also suitable for use in the present invention as are combinations of one or more protein, nucleic acid or polysaccharide.

The molecular weight of the biologically active material should preferably not be greater than about 20,000 Da. This is because, even with the increased permeability of the cells which comes about as a result of the use of the compositions of the present invention, it is no easy matter to achieve effective bioavailability with active molecules of greater size than this. In general, however, the smaller the size of the active molecule, the easier it becomes to deliver and it is therefore preferred that the biologically active molecule has a molecular weight of less than about 10,000 Da and, most suitably, less than about 5,000 Da.

The amount of biologically active material present will naturally depend on its intrinsic potency. All that is necessary is that it is present in a sufficient amount that it manifests its desired activity when ingested. For pharmaceuticals, the amount administered will be under the guidance of the physician or clinician.

Other excipients which may be present include lactose, employed as a filler, to ensure homogeneity of the composition, and to aid in handling of the preparation, Ac-di-sol™ (cross-carmellose sodium), a swelling agent which aids tablet disintegration, and polyvinyl pyrollidone, commonly used as a binding agent during granulation processes.

The formulation will usually be in a solid or, exceptionally, liquid form. Solid forms are preferred because the active material can easily be prevented from being digested in the stomach by enteric coating, and it is much easier to ensure that the active ingredient(s) and the bile salt reach the small intestine both intact and contemporaneously; this is much more difficult to achieve with a liquid formulation. If the composition is formulated as a solid, which should, for a prolonged shelf life, be substantially dry, it may be in tablet, bolus, powder, granular or microgranular form and may also contain appropriate fillers or binders which are well known to those skilled in the art. Powders, granules or microgranules may be encapsulated. As mentioned above, either a bile acid or a bile salt may be used in a solid formulation.

Liquids suffer from the disadvantages referred to above. However, if for any reason it is particularly desired to formulate a composition of the invention as a liquid, an enteric coated capsule is probably the best means of administration of the contents, which may be a syrup or elixir.

The compositions may be formulated for rapid or sustained release or a combination of these two release forms may be used. The compositions can also be incorporated into immediate, delayed or pulsed release formulations. The amount of buffering agent included in the composition will be dependent upon the way in which the composition is formulated and the time taken for it to disperse in the gut and thus the amount of buffering agent included in a sustained release formulation will generally be much greater than the amount needed for a rapid release formulation.

In general the compositions of the invention may be prepared simply by admixing the ingredients using techniques well known to those skilled in the art of preparing pharmaceutical formulations.

The invention also relates to a method of improving the bioavailability of an active material, the method comprising coadministering to a patient an active material, a bile salt and an agent adapted to adjust the gut to a pH of from 7.5 to 9.

Therefore, in a second aspect of the invention there is provided the use of a bile salt and an agent adapted to adjust the gut to a pH of from 7.5 to 9 in the preparation of an agent for increasing the bioavailability of a biologically active material to be coadministered with the agent.

Preferred features are as detailed for the first aspect of the invention, mutatis mutandis.

The invention will now be further described with reference to the following examples and to the drawings in which.

Preparation of Solutions for Use in Examples

A neutral red stock solution was prepared at concentration of 0.5 mg/ml in DMEM (Dulbecco's Modified Eagle Medium) (pH 4.5) which was then diluted 1:10 with TCM (Tissue Culture Medium) or Hanks Balanced Salt Solution (HBSS) before use.

Hanks Balanced Salt Solution (HBSS) was prepared containing the following ingredients:

|  | g/L | mM |
|---|---|---|
| $CaCl_2.2H_2O$ | 0.19 | 1.26 |
| KCl | 0.40 | 5.37 |
| $KH_2PO_4$ | 0.06 | 0.44 |
| $MgCl_2.6H_2O$ | 0.10 | 0.49 |
| $MgSO_4.7H_2O$ | 0.10 | 0.41 |
| NaCl | 8.00 | 133.33 |
| $NaHCO_3$ | 0.35 | 4.17 |
| $Na_2HPO_4$ | 0.48 | 3.38 |
| D-Glucose | 1.00 | 5.56 |
| Phenol Red | 0.01. |  |

A 0.1M solution of sodium bicarbonate in distilled water was prepared (buffer solution). Similar 0.1M solutions of sodium acetate, sodium borate and sodium carbonate in distilled water were also prepared. These are also referred to in the examples as buffers.

Test solutions were prepared containing various concentrations of a bile salt in either HBSS or in one of the 0.1M buffer solution. The following bile salts were tested:

Unconjugated Bile Salts: sodium cholate, sodium ursodeoxycholate, sodium chenodeoxycholate, sodium deoxycholate;

Conjugated Bile Salts: sodium taurocholate, sodium glycocholate, sodium taurodeoxycholate, sodium glycodeoxycholate.

A MTT stock solution was prepared at a concentration of 5 mg/ml in distilled water, which was then diluted 1:10 with TCM before use.

The tests described in Examples 1 and 2 are well known tests and conform to British Standards (BS 5750). Caco-2 cells are well recognised by those skilled in the art to be the best available in vitro model for intestinal cells.

EXAMPLE 1

In Vitro Culture Experiments for Determination of Cytotoxicity and Cell Membrane Permeability
Preparation of Cells Test plates were set up by aliquotting 200 µl of a Caco-2 cell suspension containing $1 \times 10^5$ cells/ml into each well of a 96-well microtitre plate. The outermost wells were filled with 200 µl saline alone, to counteract the effects of evaporation. The cells were incubated in high glucose Dulbecco's modified eagles medium (DMEM) tissue culture medium (TCM) at 370° C., 5% $CO_2$ in air, for 8 days, with feeding where necessary. The cells were then used for performance of either an initial insult or a recovery study.

A. Assessment of Toxicity Upon Initial Insult

Neutral red stain is actively taken up by viable cells. Cells with more permeable membranes will lose stain into the bathing medium and thus cell membrane permeability can be directly assessed after exposure to the test material by quantifying the stain remaining in the cell. In this procedure, therefore, cells are first stained and then incubated with test materials and measurements are made to determine the extent to which incubation with test materials has caused the stain to leak out of the cells during exposure. An exposure duration of 2 hours was used and the experiment was conducted according to the following protocol.

TCM was removed from cell monolayers in each well and replaced with 200 µl of stain. The plates were incubated for 2 hours at 37° C., 5% $CO_2$, and then checked for even staining and normal morphology. Stain was removed from each well and replaced with 150 µl of the appropriate buffer. Buffer was removed from wells in column 2 and replaced with 150 µl of test solutions at the highest concentration. 150 µl of test solutions was added to each of wells in column 3, mixed gently by aspiration repeatedly, and 150 µl transferred to wells in column 4. This process was repeated down the plate to obtain two-fold serial dilutions of test material along each row. One row on each plate was allocated to HBSS as a control, and one row for a buffer control if necessary.

The cells were incubated for 2 hours at 37° C. in 5% $CO_2$. The stain was then aspirated from the wells and the plates incubated with shaking for 20 minutes in desorbing solution (100 µl/well) consisting of 1% glacial acetic acid in 50% ethanol.

In order to quantify the amount of stain remaining in the cells, absorbances were measured on a plate reader at 550 nm, and readings compared with buffer controls to assess leakage of the stain from the cells.

The test is thus used as a measure of cell membrane permeability at the time of exposure to bile salts.

B. Recovery from Toxic Insult

Neutral red stain is actively taken up by viable cells and non-viable cells will not stain. Cells with increased cell membrane permeability will have a reduced stain content. In this variant of the procedure, cells are first incubated with test materials, then incubated with stain, and measurements are made to determine the extent to which incubation with the test materials has caused the cells to be unable to take up/retain neutral red after exposure. A 2-hour exposure period is used together with a 3-hour recovery period in optimal growth material during which stain is taken up. The following protocol was followed:

TCM was removed from each well and replaced with 150 µl of the appropriate buffer.

Buffer was removed from wells in column 2 and replaced with 150 µl of test solutions at the highest concentration.

150 µl of test solutions was added to each of wells in column 3, mixed gently by aspirating repeatedly, and 150 µl transferred to wells in column 4. This process was repeated down the plate to obtain two-fold serial dilutions of test material along each row. One row on each plate was allocated to HBSS as a control, and one row for a buffer control if necessary. The cells were incubated for 2 hours at 37° C. in $CO_2$.

The supernatant liquid was then removed from cell monolayers in each well and replaced with 200 µl of stain.

The plates were incubated for 3 hours at 37° C., 5% $CO_2$. The stain was then aspirated from the wells and the plates were then incubated with shaking for 20 minutes in desorbing solution (100 µl/well) consisting of 1% glacial acetic acid in 50% ethanol.

Absorbances were measured on a plate reader at 550 nm, and readings compared with buffer controls to assess leakage of neutral red out of the cells after active uptake of the stain.

The test is thus used as a measure of cell membrane permeability during the recovery period after exposure to bile salts.

Figure 2:
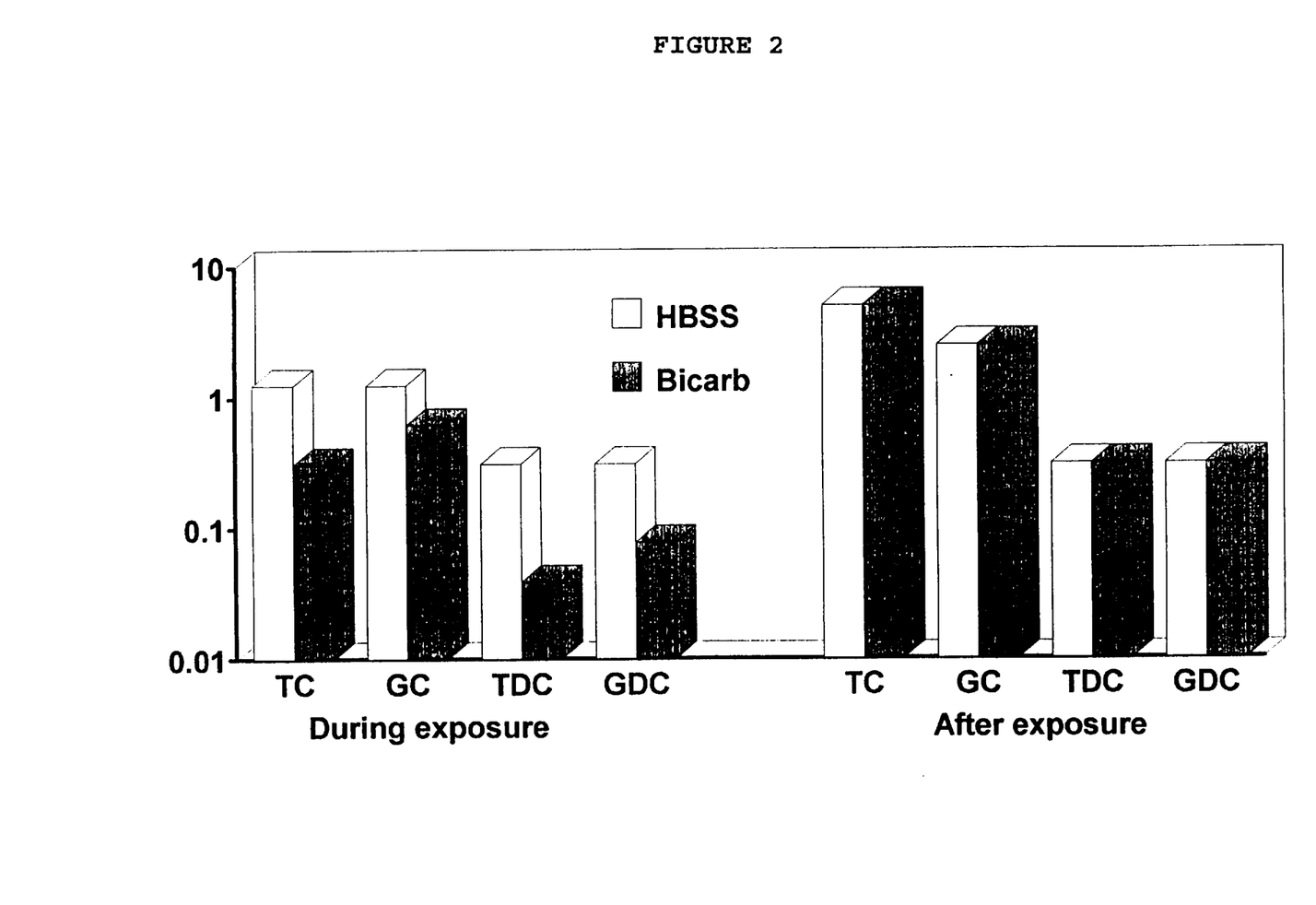
FIG. 2 shows a comparison of neutral red permeability of Caco-2 cells in vitro during and after exposure to conjugated bile salts in either HBSS or bicarbonate solution, the results being expressed as maximum tolerated concentrations of bile salt in mg/ml.
Figure 3:
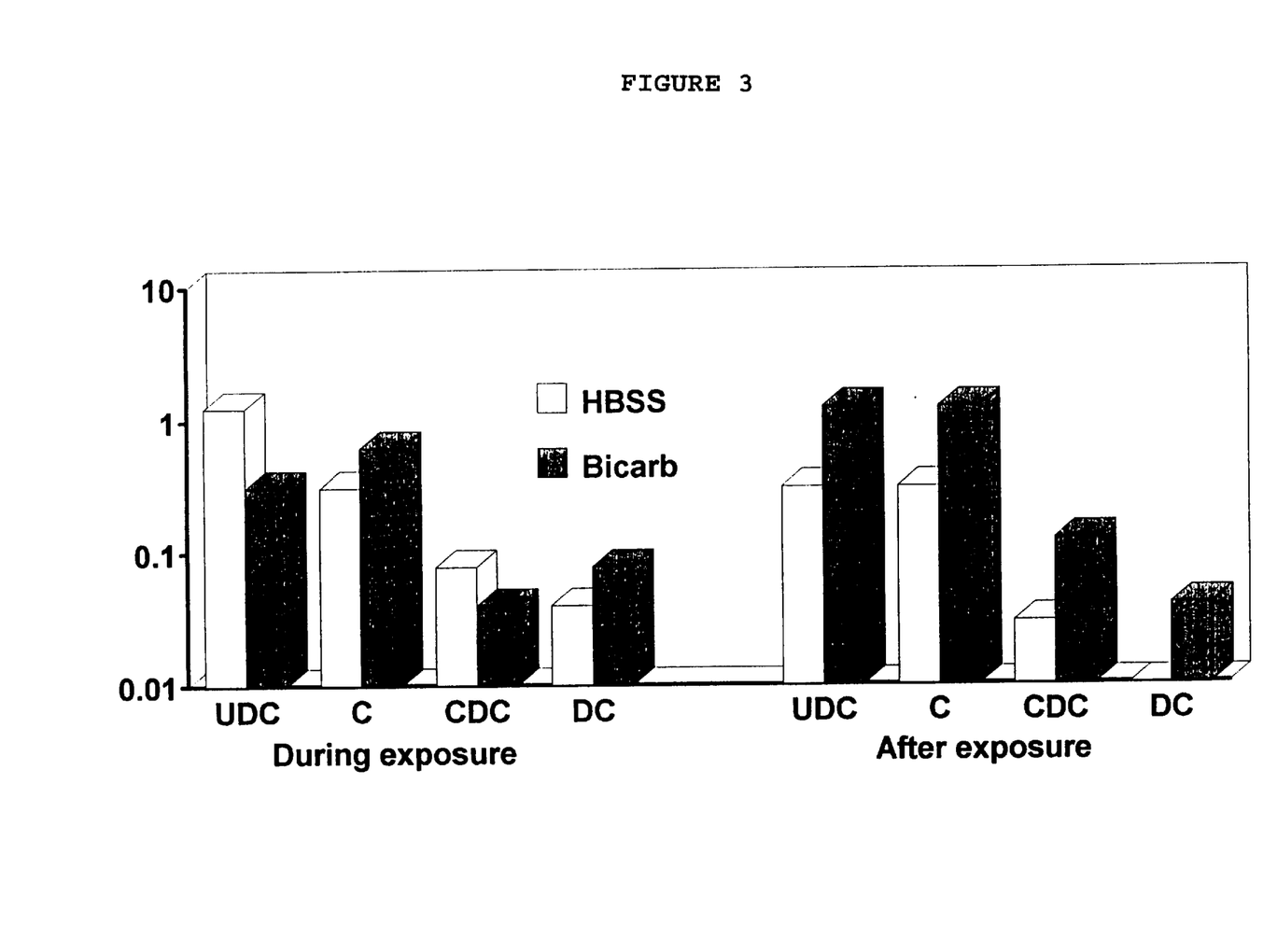
FIG. 3 is a comparison of neutral red permeability of Caco-2 cells in vitro during and after exposure to unconjugated bile salts in either HBSS or bicarbonate solution, the results being expressed as maximum tolerated concentrations of bile salt in mg/ml.

A comparison of the effects of bicarbonate and HBSS on cells treated with bile salts is set out in Tables 1 and 2 and FIGS. 2 and 3. The effects of HBSS and bicarbonate, acetate and borate buffers are compared in FIGS. 4 and 5.

It should be noted that in HBSS the proportions of the components have been adjusted so as to achieve pH of 7.0 to 7.2 when dissolved together in distilled water. In the small intestine, the pH will be lower than this.

With 0.1M bicarbonate, in contrast, as may be seen from the table given earlier, the pH will be close to pH 8.0, and was confirmed to be so at the end of each of the experiments described here.

EXAMPLE 2

In Vitro Culture Experiments for Determination of Cytotoxicity Using MTT Staining for Mitochondrial Activity Preparation of Cells Test plates were set up by aliquotting 200 µl of a Caco-2 cell suspension containing $1 \times 10^5$ cells/ml into wells of a 96-well microtitre plate. The outermost wells on each plate were left blank, and filled with 200 µl saline, to counteract the effects of evaporation. The cells were is incubated in high glucose DMEM tissue culture medium (TCM) at 37° C., 5% $CO_2$ in air, for 8 days, with feeding when necessary.

Test for Mitochondrial Activity

MTT is a tetrazolium salt which is converted by mitochondrial dehydrogenases in viable cells to form an insoluble purple crystal. Dead cells would not effect this conversion. Crystal formation can be quantified colorimetrically and used to asses mitochondrial activity and therefore cell viability. The preparation of MTT stock solution, test solutions and buffer solution is described above.

In this procedure, cells are first incubated with test materials and then incubated with MTT and measurements are made to determine the extent to which incubation with test materials has altered the mitochondrial activity of the cells. A two hour exposure period is used together with a three hour recovery period during which time staining is conducted.

TCM was removed from each well and replaced with 150 Al of the appropriate buffer.

Buffer was removed from wells in column 2 and replaced with 150 μl of test solutions at the highest concentration.

150 μl of test solutions was added to each of wells in column 3, mixed gently by aspirating repeatedly, and 150 μl transferred to wells in column 4. This process was repeated down the plate to obtain two-fold serial dilutions of test material along each row. One row on each plate was allocated to Hanks Balanced Salt Solution (HBSS—See Example 1) as a control, and one row for a buffer control if necessary. The cells were incubated for two hours at 37° C. in 5% $CO_2$.

The cells were incubated for 2 hours at 37° C. in 5% $CO_2$. The supernatant liquid was then removed from cell monolayers in each well and replaced with 200 μl of MTT.

The plates were incubated for 3 hours at 37° C., 5% $CO_2$, and the wells examined to assess the level of staining by eye. The stain was then aspirated from the wells and the plates were incubated with shaking for 20 minutes in desorbing solution (100 μL/well) consisting of 0.1M HCl in anhydrous isopropanol.

Absorbances were measured on a plate reader as the difference between 550 and 650 nm, and readings compared with buffer controls to assess change in mitochondrial activity. A reduction in staining below that for controls indicates a reduction in mitochondrial activity, and is highly indicative of a toxic action of materials in the incubation medium.

RESULTS

The results of Examples 1 and 2 are set out in Tables 1 and 2, and FIGS. 1 to 5 which illustrate the effects exerted by conjugated and unconjugated bile acids in the presence of high pH buffers, using bicarbonate as a particular example.

TABLE 1

Maximum Concentration of Unconjugated Bile Salt (mg/mL) Tolerated by Caco-2 Cells In Vitro in the Presence of Either Bicarbonate or HBSS

| Bile Salt | Test Medium | Neutral Red (During) | Neutral Red (After) | MTT Viability (After) |
| --- | --- | --- | --- | --- |
| Cholate | HBSS | 0.313 | 0.313 | 0.313 |
| | Bicarb. | 0.625 | 1.25 | 2.5 |
| Ursodeoxycholate | HBSS | 1.25 | 0.313 | 0.625 |
| | Bicarb. | 0.313 | 1.25 | 1.25 |
| Chenodeoxycholate | HBSS | 0.078 | 0.03 | 0.125 |
| | Bicarb. | 0.04 | 0.125 | 0.25 |
| Deoxycholate | HBSS | 0.04 | 0.01 | 0.01 |
| | Bicarb. | 0.078 | 0.04 | 0.156 |

TABLE 2

Maximum Concentration of Conjugated Bile Salt (mg/mL) Tolerated by Caco-2 Cells In Vitro in the Presence of Either Bicarbonate or HBSS

| Bile Salt | Test Medium | Neutral Red (During) | Neutral Red (After) | MTT Viability (After) |
| --- | --- | --- | --- | --- |
| Taurocholate | HBSS | 1.25 | 5 | 5 |
| | Bicarb. | 0.313 | 5 | 5 |
| Glycocholate | HBSS | 1.25 | 2.5 | 2.5 |
| | Bicarb. | 0.625 | 2.5 | 2.5 |
| Taurodeoxycholate | HBSS | 0.313 | 0.313 | 0.313 |
| | Bicarb. | 0.039 | 0.313 | 0.313 |
| Glycodeoxycholate | HBSS | 0.313 | 0.313 | 0.313 |
| | Bicarb. | 0.078 | 0.313 | 0.313 |

Tables 1 and 2 show the results of the experiments described in Examples 1 and 2. The first columns of the tables list the bile salts which were present in the test media and the test media themselves are set out in the second column. The test medium was either HBSS or the 0.1M sodium bicarbonate solution.

The results for the neutral red assays during and after exposure to bile salt give the maximum concentration of bile salt in mg/mL at which the permeability of the cell remains unaffected compared with cells incubated in medium with no bile salt) . The results in the MTT column represent the maximum concentration of bile salt at which the viability of the cell remained unaffected after incubation.

Table 1 gives the results for the unconjugated bile salts and shows that, in each case, the figures in the Neutral Red (After Exposure) and MTT column are higher for the bile salts administered with bicarbonate than for those administered with HBSS although there is no significant difference in the figures in the Neutral Red (During Exposure) column. This indicates that the permeability of the cells during incubation with the bile salt solution is not greatly changed in the presence of bicarbonate ions, but that a great deal more bile salt is needed for a toxic effect to be apparent in the cells after incubation. Effectively this means that cells can be exposed to a much greater amount of bile salt when in the presence of bicarbonate ions before a toxic effect on the cells becomes apparent. Because it is possible to increase the amount of bile salt, the permeability of the cells after incubation can also be increased without affecting the viability of the cells.

Table 2 gives the results for the conjugated bile salts and shows that, in each case, the figures in the Neutral Red (During Exposure) column are increased when the bile salt is administered in the presence of bicarbonate while the figures in the Neutral Red (After Exposure) and MTT columns are the same. This indicates that much less bile salt is needed to increase the permeability of the cells when they are incubated with bile salts in the presence of bicarbonate than when bicarbonate is not present.

The results also show that the permeability and viability of the cells after incubation is not affected by the presence of the bile salt. Thus, in the presence of bicarbonate ions, it is possible to increase the permeability of cells during incubation with conjugated bile salts without increasing the bile salt concentration and thus without adversely affecting the viability of the cells.

Figure 1:
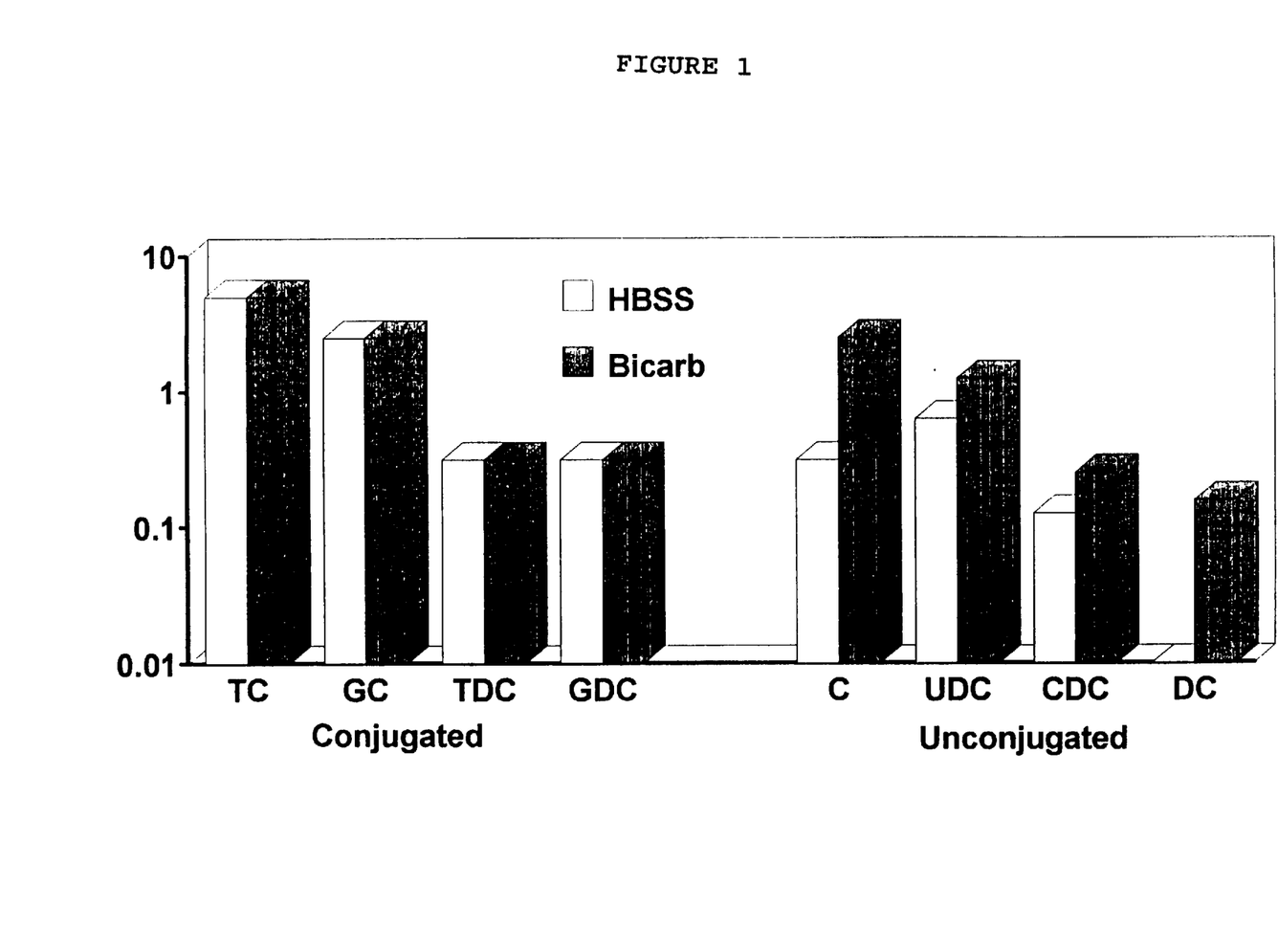
FIG. 1 shows a comparison of the viability of Caco-2 cells after exposure to bile salts in vitro in either balanced salt or bicarbonate solution, the results being expressed as maximum tolerated concentrations of bile salt in mg/ml.

FIGS. 1 to 3 are graphical representations of the results presented in Tables 1 and 2. FIG. 1 shows the effect of bicarbonate on the viability of cells incubated with bile salt solutions as measured by the MTT viability test. For conjugated bile salts, it can be seen that the presence of bicarbonate does not affect the viability of the cells after incubation with the bile salt but for the unconjugated bile salts, the concentration of bile salt with which cells can be treated without affecting their viability is considerably increased in the presence of bicarbonate.

FIG. 2 shows the results for cell permeability as measured by the neutral red assay both during and after incubation with conjugated bile salts. It can be seen that during exposure, the amount of bile salt needed to increase the permeability of cells is considerably lower in the presence of 0.1M bicarbonate than in the presence of HBSS. However, after exposure, the permeability of the cells returns to normal. This means that for a given amount of bile salt, cell permeability can be significantly increased during exposure. However, after exposure, the viability of the cells remains unchanged with reference to control (cells incubated with bile salts and HBSS with no bicarbonate).

FIG. 3 is similar to FIG. 2 but in this case the results for unconjugated bile salts are presented. In this case it can be seen that bicarbonate has no clear cut effect on the permeability of the cells during exposure to the bile salt but that after exposure, the maximum concentration of bile salt which can be administered without causing an increase in cell permeability is increased and thus the cell permeability is significantly decreased in the presence of bicarbonate.

Figure 4:
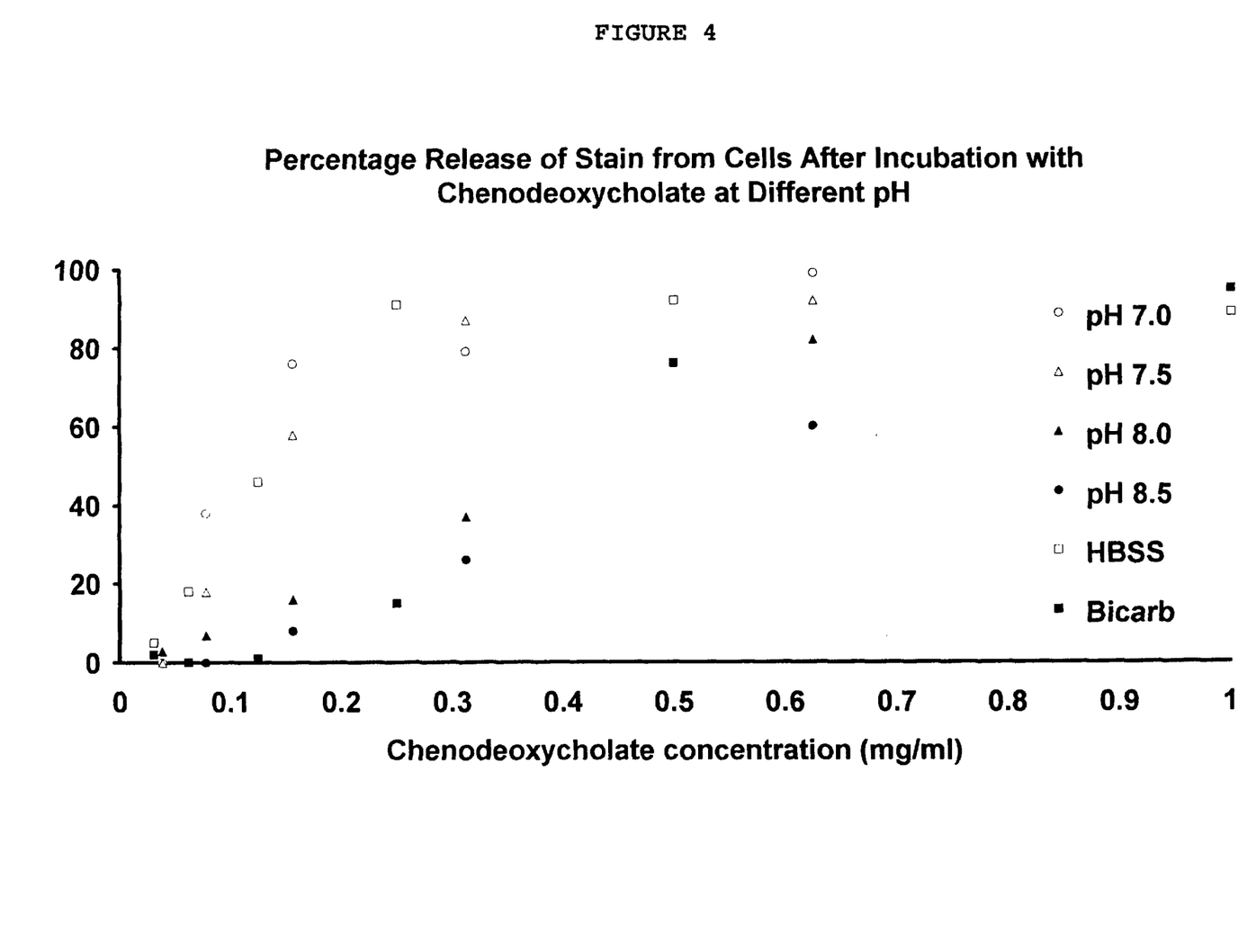
FIG. 4 is a plot showing the percentage release of stain after incubation of stained cells with chenodeoxycholate in different buffers.
Figure 5:
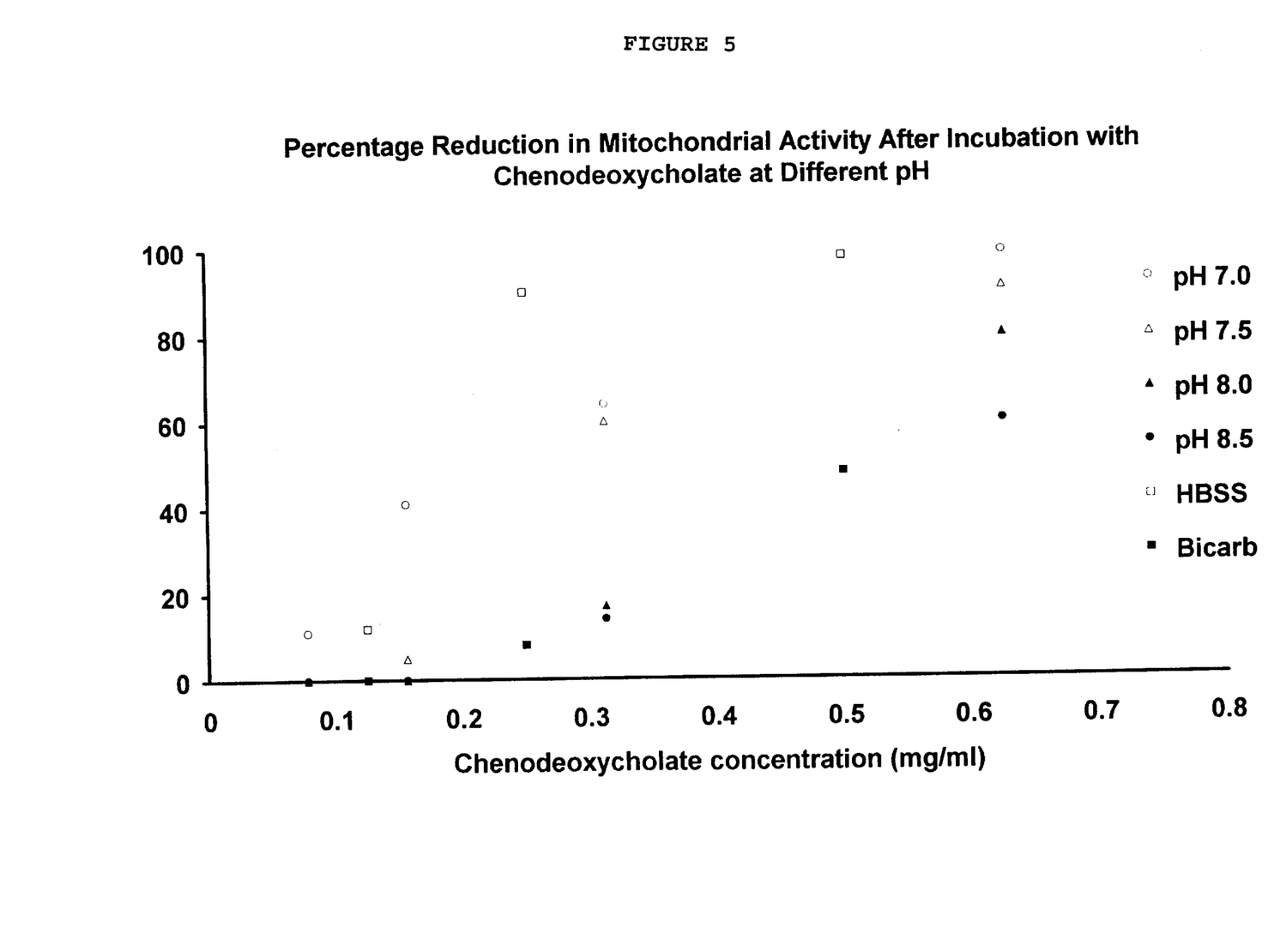
FIG. 5 is a plot showing the percentage reduction in mitochondrial activity after incubation with chenodeoxycholate in different buffers.

FIG. 4 is a plot showing the percentage release of stain in the neutral red recovery assay after exposure of stained cells to bile salt at different pH values, using chenodeoxycholate as an example. This plot shows quite clearly that much less stain is released from cells which have been incubated at pH above 7.5, and this is an indication that the prospects for both short- and long-term recovery of the cells are much better under conditions of elevated pH. Similarly, FIG. 5, which is a plot showing the percentage reduction in mitochondrial activity after incubation with chenodeoxycholate in different buffers, indicates that a marked reduction in toxicity is achieved under conditions of elevated pH.

The pH 7.0 medium was prepared using HBSS containing 3% (v/v) 1M HEPES (hydroxyethyl propylidene ethane sulphonic acid) solution adjusted to pH 7.0. The pH 7.5 medium was prepared using HBSS containing 50 mM TRIZMA™, and adjusted to pH 7.5. The pH 8.0 medium was prepared using HBSS containing 50 mM TRIZMA™, and adjusted to pH 8.0. The pH 8.5 medium was prepared using HBSS containing 50 mM Tricine, and adjusted to pH 8.5. The results also indicate that this phenomenon is observed with 0.1M bicarbonate at pH 8.0, but not with HBSS alone at pH 7.0.

Confirmation that the concentrations of bicarbonate used do indeed have the desired effect in the gut milieu is obtained in the in vivo experiments reported in the following examples.

EXAMPLE 3

In vivo Efficacy Study—Salmon Calcitonin

Pigs (large white×large white/landrace, male, 65 kg) were employed for the study and were surgically prepared ten days before commencement by implantation, under anaesthesia, of two catheters in the dorsal aorta via the median saphenous arteries. A cannula of approximately 1.6–2mm internal diameter was implanted in the jejunum. Animals were provided with water ad lib, fasted overnight, and fed twice daily in the morning and evening. On days of treatment, the morning feed was withheld until after the taking of the last blood sample.

Dosing of salmon calcitonin (sCT) was administered by instillation via the indwelling cannula into the jejunum, followed by flushing with warm sterile water. 8 ml blood samples were removed at various times before and after dosing, and divided into two portions. One portion was allowed to clot at room temperature, and the serum removed and stored at −20° C. until ready for use. The other portion was transferred to heparinised tubes to which 4000 kiu aprotinin was added, and the plasma decanted after centrifugation and stored at −20° C. Serum calcium levels were measured colorimetrically after complexation with the calcium-sensitive chelating agent arsenazo III.

Figure 6:
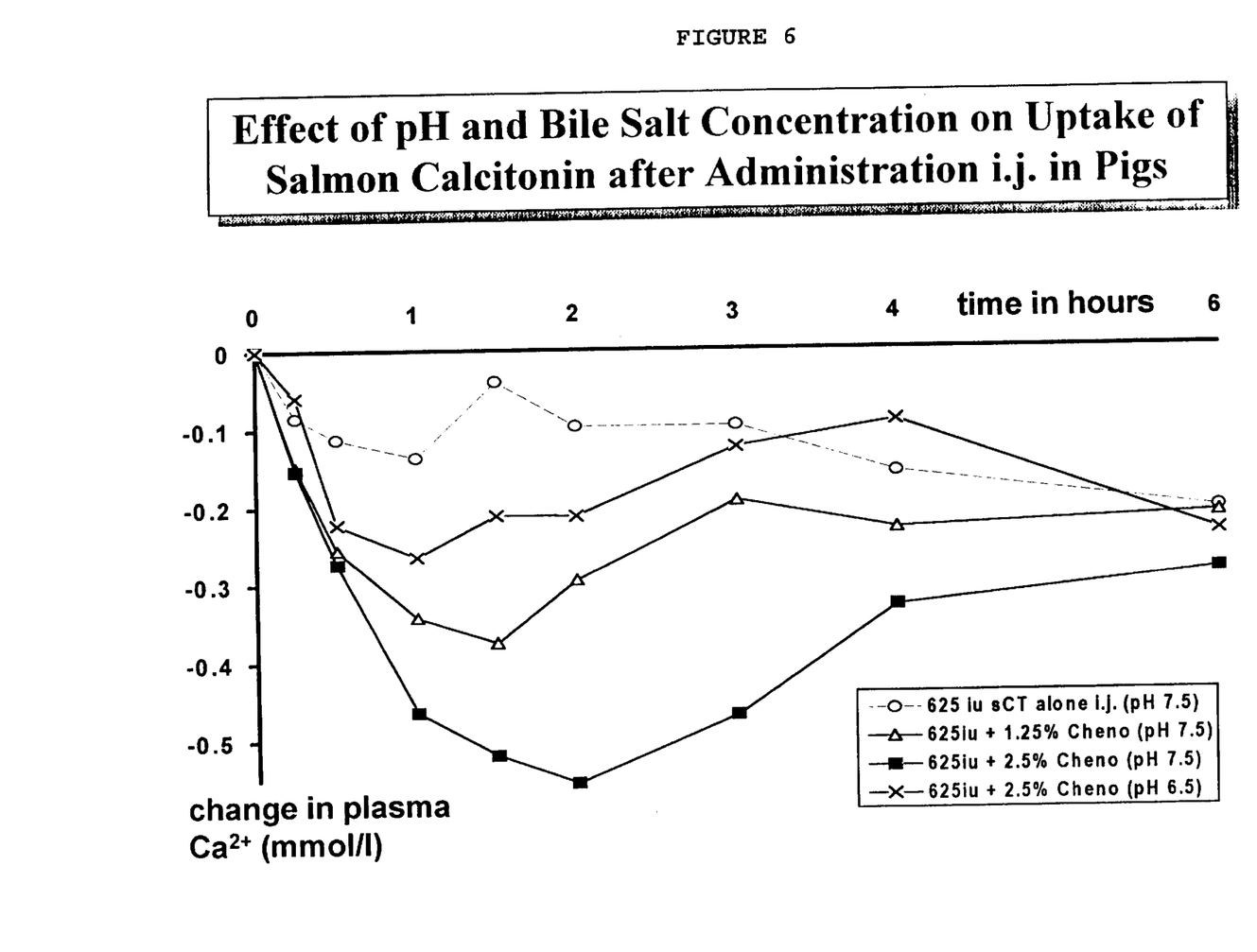
FIG. 6 is referred to in Example 3 and shows the effect of pH and bile salt concentration on uptake of salmon calcitonin (SCT) after administration intrajejunally in pigs.

Nine animals were used in the study, and formulations were administered on three separate days, each separated by at least one day, on a random three-way crossover basis, so that all pigs received all three treatments. Each of the treatments consisted of 625 iu of sCT dissolved in 2 ml of phosphate-buffered saline at pH 7.5, either alone (-o-), together with 25 mg of sodium chenodeoxy cholate (-Δ-), together with 50 mg of sodium chenodeoxy cholate (-■-), or with 50 mg of sodium chenodeoxy cholate where the pH was subsequently brought down to 6.5 with hydrochloric acid (-x-). The results are shown in FIG. 6 and are expressed as variations in plasma calcium concentration with time due to calcitonin, from which it can be seen that the efficacy of bile salts in enhancing uptake of calcitonin is dependent on the concentration of bile salt present, and the pH at which it is administered.

EXAMPLE 4

In vivo Efficacy Study Insulin

Pigs prepared in an identical manner to that described in Example 3 were employed. Blood samples taken were analysed for glucose using standard enzyme-based methodology.

Animals were dosed with a solution of 200 iu insulin in 2 ml (at pH 5 to bring the peptide into solution), or with insulin formulated as a solid dose, either with or without sodium bicarbonate. Each dose contained 300 mg of either formulation, suspended rapidly in 2 ml of phosphate-buffered saline immediately prior to administration. The composition of the two formulations is listed below on a weight-for-weight basis.

| Without bicarbonate (wt/wt) | | With bicarbonate (wt/wt) | |
| --- | --- | --- | --- |
| Bovine insulin | 2.4 | Bovine insulin | 2.4 |
| Chenodeoxycholic acid | 16.7 | Chenodeoxycholic acid | 16.7 |
| Lactose | 74.9 | Lactose | 66.6 |
| Ac-di-sol | 3.0 | Ac-di-sol | 3.0 |
| Polyvinyl pyrollidone | 3.0 | Polyvinyl pyrollidone | 3.0 |
| pH | <7.0 | Sodium bicarbonate | 8.3 |
| | | pH | >7.5 |

Figure 7:
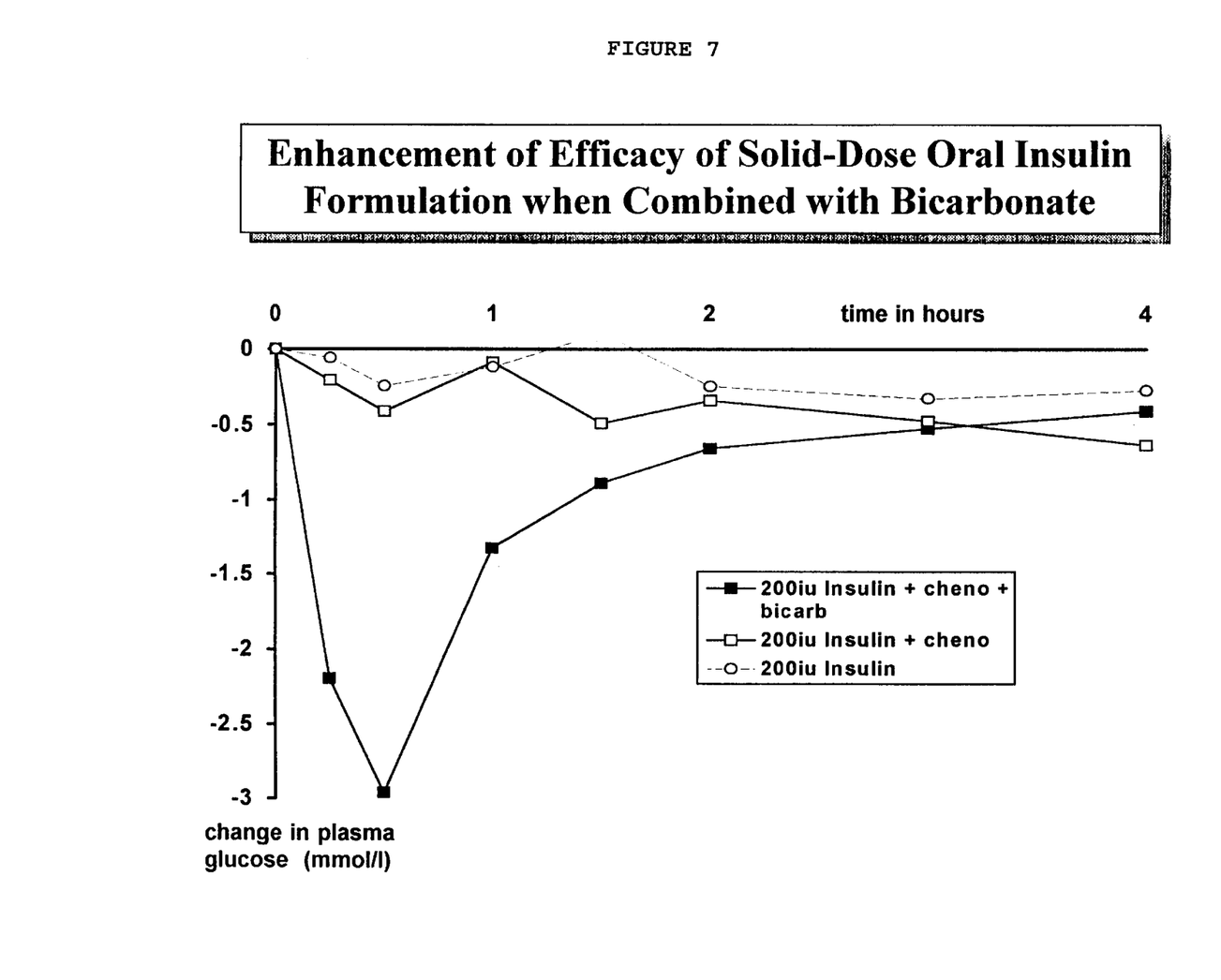
FIG. 7 is referred to in Example 4 and shows the enhancement of efficacy of solid dose oral insulin formulation when combined with bicarbonate.

The results are shown in FIG. 7, and are expressed as variations in plasma glucose concentration with time due to insulin, from which it can be seen that the efficacy of the bile acid chenodeoxycholic acid in enhancing uptake of peptide across the gut is markedly improved by the presence of sodium bicarbonate in the solid dose formulation.

We claim:

1. A pharmaceutical and/or veterinary composition comprising:

(i) a biologically active proteinaceous material, oligonucleotide or analogue thereof or polysaccharide;

(ii) a bile acid or salt; and (iii) an agent having the ability to adjust the pH of the gut to a value of from 7.5 to 9.

2. A composition as claimed in claim 1, wherein the agent has the ability to adjust the pH of the gut to a pH value of from 7.8 to 8.3.

3. A composition as claimed in claim 1 or 2, wherein a soluble counter ion is present.

4. A composition as claimed in claim 1 or 2, wherein the bile acid or salt is unconjugated.

5. A composition as claimed in claim 4, wherein the bile acid or salt is chenodeoxycholic acid or ursodeoxycholic acid or a salt thereof.

6. A composition as claimed in claim 1 or 2, wherein the bile acid or salt is conjugated.

7. A composition as claimed in claim 1, wherein the buffering agent comprises carbonate and/or bicarbonate ions.

8. A composition as claimed in claim 7 which contains sufficient bicarbonate or carbonate ions to give a concentration of at least 0.045M when a unit dose is dispersed in 10 ml of water.

9. A composition as claimed in any one of claims 1 or 2, wherein the pH adjusting agent itself comprises a bile acid or salt.

10. A composition as claimed in any one of claims 1 or 2, which includes a chelator of calcium ions which is a salt of a di- or tri-carboxylic acid or a polyphosphate such as phytate.

11. A composition as claimed in any one of claims 1 or 2, wherein the biologically active material is insulin, calcitonin, a growth hormone, an interferon, an interleukin or an active fragment of any of these.

12. A composition as claimed in any one of claims 1, or 2, wherein the molecular weight of the biologically active material is less than about 20,000 Da.

13. A composition as claimed in claim 12, wherein the molecular weight of the biologically active material is less than about 10,000 Da.

14. A composition as claimed in any one of claims 1 or 2 which is formulated as a dry solid.

15. A composition as claimed in claim 14, which is in tablet, bolus, powder, granule or microgranule form.

16. A method for preparing a preparation for use in increasing the bioavailability of a biologically active material, comprising combining a bile salt and an agent having the ability to adjust the pH of the gut to a pH value of from 7.5 to 9, said preparation suited for increasing bioavailabilty of a biologically active material to be coadministered with the agent.

17. A method of improving the bioavailability of an active material, the method comprising coadministering to a patient an active material, a bile salt and an agent having the ability to adjust the pH of the gut to a pH value of from 7.5 to 9.

18. A method for improving the effective therapeutic index of a bile salt which acts as a permeation enhancer for a bioactive material in the gut, the method comprising coadministering to a patient an active material, a bile salt and an agent having the ability to adjust the pH of the gut to a pH of from 7.5 to 9.

19. A composition as claimed in claim 10 wherein the salt is selected from the group consisting of a citrate salt, an ethylenediaminetetraacetic acid salt and an ethylene glycol bis-(β-aminoethylether)-N,N,N',N'-tetraacetic acid salt.

* * * * *